United States Patent [19]

Siedband

[11] Patent Number: 5,308,988
[45] Date of Patent: May 3, 1994

[54] ANALYZER FOR RADIOTHERAPY RADIATION BEAM

[75] Inventor: Melvin P. Siedband, Madison, Wis.

[73] Assignee: Radiation Measurements, Inc., Middleton, Wis.

[21] Appl. No.: 883,984

[22] Filed: May 18, 1992

[51] Int. Cl.⁵ .......................... G01T 1/185; H01J 47/04
[52] U.S. Cl. .................................................. 250/385.1
[58] Field of Search ..................................... 250/385.1

[56] References Cited

U.S. PATENT DOCUMENTS

| | | | |
|---|---|---|---|
| 2,953,702 | 9/1960 | Zieler | 313/93 |
| 4,365,161 | 12/1982 | Dalton et al. | 378/99 |
| 4,935,950 | 6/1990 | Ranallo et al. | 378/207 |
| 4,970,398 | 11/1990 | Scheid | 250/374 |
| 5,006,714 | 4/1991 | Attix | 250/368 |
| 5,025,376 | 6/1991 | Bova et al. | 364/413.26 |
| 5,041,730 | 8/1991 | Attix | 250/385.1 |

Primary Examiner—Constantine Hannaher
Attorney, Agent, or Firm—Quarles & Brady

[57] ABSTRACT

A radiation detector has a number of ionization chambers. Each ionization chamber is connected to an accumulating capacitor which in turn is sequentially read by a multiplexed charge-counter. The charge-counter eliminates the effect of variations of the capacitance values of the accumulating capacitors associated with each ionization chamber cell and provides a consistency of measurement among the ionization chamber cells unlike a design employing multiple measurement circuits dedicated to each ionization chamber cell.

9 Claims, 2 Drawing Sheets

ANALYZER FOR RADIOTHERAPY RADIATION BEAM

BACKGROUND OF THE INVENTION

1. Field of the Invention

This invention relates generally to radiation therapy equipment for the treatment of tumors or the like with a radiation beam, and in particular to a detector array used with such equipment for precisely characterizing the intensity of the radiation beam over an irradiated area.

2. Background Art

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue is minimized.

External-source radiation therapy uses a radiation source that is external to the patient, typically either a radioisotope, such as $^{60}$Co, or a high powered x-ray source, such as a linear accelerator. The external source produces a collimated beam directed into the patient toward the tumor site.

Determining the radiation profile of the external radiation beam (i.e., the variation in intensity over the area of the beam) is important in planning the radiation therapy, or verifying assumptions concerning beam homogeneity. The ability to accurately characterize the beam profile also permits evaluation of any filters or attenuating blocks that may be used in conjunction with the radiation beam to control and attenuate the radiation beam.

Several methods are currently used to determine the intensity of a radiation beam over an exposed area. In one method, a tank of water simulates patient absorption and a small radiation detector, typically an ionization chamber, is driven to different positions within the tank while measurements are made. The ionization chamber generates a current between two charged electrodes, an anode and cathode, as conducted by atoms of a gas held in a cell between the electrodes and ionized by the radiation.

In order to have sufficient resolution in the measurement of the radiation beam, a number of locations in the beam must be sampled and the detector must be small. But the movement of the detector to each measurement point is time consuming and the small detector requires a significant period of time at each measurement point to collect enough energy to ensure precise measurement of the radiation intensity. The extended time required to collect these measurements may be inconvenient and may tax the operating limits of the radiation source (particularly, a linear accelerator) which must be active for a longer period of time than is usual for treatment. The setting up and taking down of the water tank used with this procedure, is also inconvenient.

A second method of determining the intensity of a radiation beam over an area uses multiple ionization chambers to characterize the beam at numerous measurements points simultaneously. Each ionization chamber is equipped with its own integration and amplification circuitry to provide a signal indicating the total radiation received. The circuit components must be closely matched to ensure comparable readings from each of the multiple ionization chambers. For large numbers of ionization chambers, this matching becomes difficult and the detector becomes quite expensive.

SUMMARY OF THE INVENTION

The present invention provides a detector using multiple ionization chambers to provide rapid measurement of a radiation beam without the problems associated with constructing a large number of matched amplifiers and integrators.

Specifically, an accumulating capacitor is connected to each ionization chamber to collect the charge produced by the ionization chamber during a sampling period. A multiplexer sequentially connects each accumulating capacitor to a charge-counter which measures the amount of charge collected on each accumulating capacitor.

It is one object of the invention to reduce the amount of circuitry necessary to support a large array of ionization chambers. The multiplexer, by sequentially scanning each ionization chamber, allows the circuitry of the charge-counter to be effectively shared among the ionization chambers. Only the relatively inexpensive accumulating capacitor must be duplicated for each ionization chamber.

It is a further object of the invention to reduce the variations in the measurement of the intensity of a radiation beam by different ionization chambers, such differences caused by variations in the measuring circuits associated with those ionization chambers. The sharing of the charge-counter circuit eliminates the need to precisely calibrate multiple charge-counters to each other and ensures consistency of measurement between the ionization chambers.

It is yet another object of the invention to minimize the effect on the measurement of a radiation beam attendant to variations in the electrical component associated with each ionization chamber. As mentioned, an accumulating capacitor is connected to each ionization chamber to store the charge from the ionization chamber between readings by the multiplexed charge-counter. The use of a charge-counter, as opposed to a voltage sensitive device, makes the precise matching of the capacitance values of the accumulating capacitors unimportant. The particular capacitance value does not significantly affect the amount of charge collected on the accumulating capacitor nor the measurement of that charge by the charge-counter.

The foregoing and other objects and advantages of the invention will appear from the following description In the description, reference is made to the accompanying drawings which form a part hereof and in which there is shown by way of illustration, a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
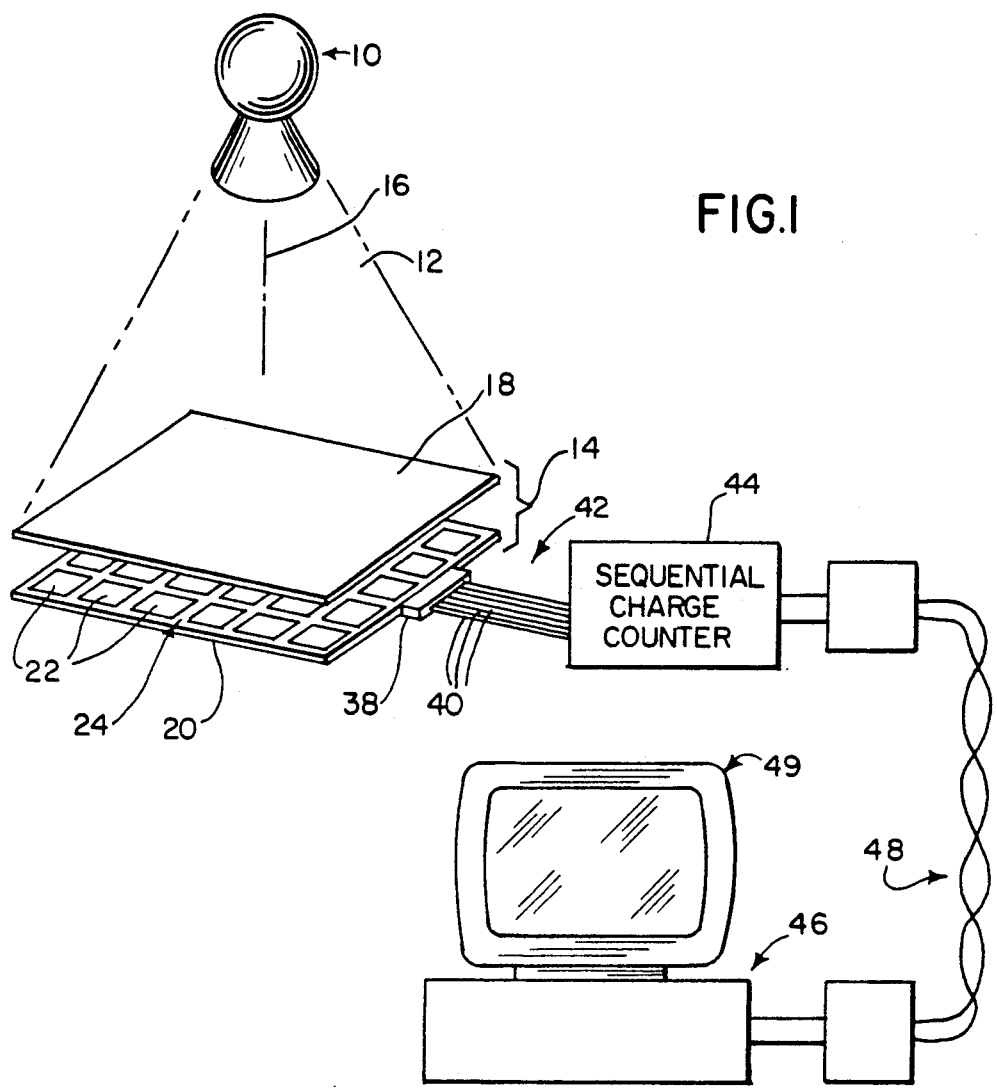
FIG. 1 is a simplified block diagram of a detector array for measuring a profile of a radiation beam per the present invention and showing a plurality of anodes defining an array of ionization chambers connected to a sequential charge-counter.

Referring to FIG. 1, a radiotherapy system, incorporating the present invention, includes a radiation source 10 directed and collimated so as to project a generally pyramidal beam of radiation 12 toward a detector array 14. The radiation beam 12 diverges symmetrically about an axis 16 having one end located at the radiation source 10 and the apex of the generally pyramidal radiation beam 12.

The detector array 14 includes a rectangular common cathode 18 subtending the radiation beam 12 at a distance from the radiation source 10 and substantially perpendicular to the axis 16. An array of anodes 20, positioned on the far side of the common cathode 18 with respect to the radiation source 10, is spaced away from the common cathode 18 by insulating supports (not shown) and the space between the common cathode 18 and the array of anodes 20 is filled with air. The surface of the array of anodes 20 facing the common cathode 18 is covered by a checkerboard pattern of square anodes 22 separated by insulating guard channels 24 as will be described below. Each anode defines a cell of a single, independent ionization chamber.

Figure 2:
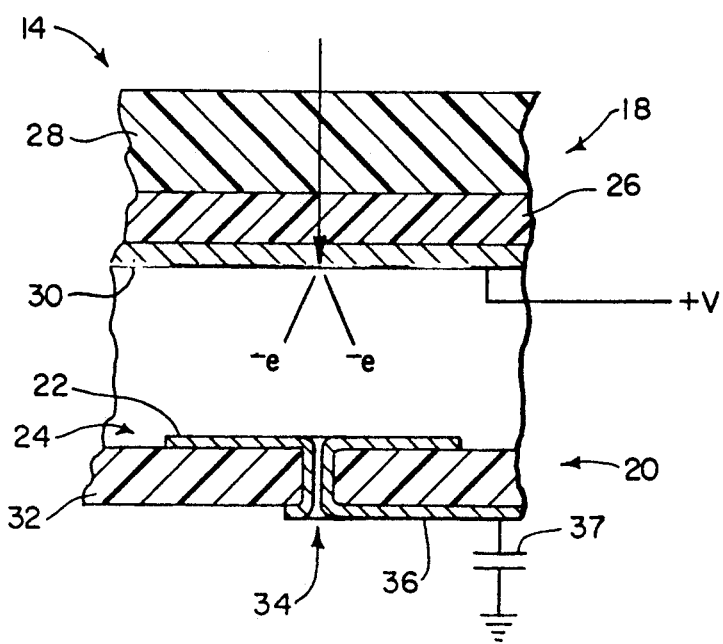
FIG. 2 is a cross section through the ionization chamber array of FIG. 1 showing the common cathode and anodes of the ionization chamber array, the latter for receiving charges developed by the interaction of the radiation beam with the material of the anode and the ionizable gas therebetween.

Referring also to FIG. 2, the common cathode 18 comprises a build-up plate 28 of approximately 0.5" of plastic material which serves to decelerate higher energy photons from the radiation 12 and increase their probability of producing conductive electrons and ions as described below. The plastic of the build-up plate 28 may be acrylic or other material having similar attenuating characteristics. Particularly suited is an attenuating material manufactured by Radiation Measurements, Inc. of Middleton, Wis. under the name "Plastic Water".

Beneath the build-up plate 28, with respect to the radiation source 10, is an insulating sheet 26 of ⅛" fiberglass such as is used for manufacturing printed circuit boards. The back surface of insulating sheet 26 is clad with a conductive copper sheet 30 which is connected to a positive voltage source, typically of approximately 300 volts. The copper sheet 30 is chosen to have a high atomic number to increase its interaction with the radiation beam 12 as will be described.

The array of anodes 20 is constructed of a similar insulating sheet 32 of epoxy fiberglass having the anodes 22 on its front surface, towards the common cathode 18. The anodes 22 are formed from a continuous copper cladding on that front surface of sheet 32 which has been etched to the checkerboard pattern by a photographic etching process such as is well known in the printed circuit industry. The photographic etching process allows a very high precision and uniformity in the dimensions of the anodes 22.

Thus, the insulating guard channels 26 separating each anode 22 from the others are areas on the front surface of the insulating sheet 32 where the copper cladding of the anodes 22 has been etched away.

A plated-through hole 34 connects each anode 22, on the front surface of the array of anodes 20, to an individual conductor 36 on the back surface of the array of anodes 20. Each conductor 36 is received separately at the edge of the array of anodes 20 by a multiconductor connector 38 which connects the conductors 36 to corresponding conductors 40 of a multiconductor cable 42 (shown in FIG. 1).

Referring still to FIG. 2, radiation of the radiation beam 12 strikes the common cathode 18 of the detector array 14 and the conductive metal 30, the latter which emits high energy electrons into the air-filled volume beneath the plates 18 and 20. The high energy electrons strike the air molecules producing ions allowing measurable current flow between the conductive metal 30 of the common cathode 18 and the anodes 22 of the array of anodes 20. This current is transmitted along the conductors 36 associated with each anode 22 to charge an accumulating capacitor 37. The charge on this accumulating capacitor 37 will be measured by a sequential charge-counter to be described in detail below and periodically may be discharged through a further extent of conductor 36 attached to connector 38. Capacitors 37 are typically Mylar capacitors that have internal time constants of several days and thus very low leakage.

Variation in intensity of the radiation 12 striking areas of the common cathode 18 over different anodes 22 causes proportionally different current flows into the anodes 22 and thus into their associated conductors 36. The total charge conveyed by the current flow will be proportional to the total radiation 12 received at a given anode 22. Accordingly, the intensity profile of the radiation beam 12 over the area of the common cathode 18 may be quantified by measuring the charge collected on the accumulating capacitors 37 associated with each anode 22 over a predetermined period of time.

Referring again to FIG. 1, the charge on each accumulating capacitor 37 is conducted, in sequence, by one conductor 40 of cable 42 to a sequential charge-counter 44. The sequential charge-counter 44 measures, one at a time, the charge collected by each capacitor 37 associated with each anode 22 as controlled by a computer 46.

The computer 46 communicates with the sequential charge-counter 44 through a Bi-directional communications link 48, such as the RS422/RS488 standards that is well known in the art. The particular communications link permits the use of two-wire telephone lines to connect a number of radiotherapy machines to a central computer through standard circuit boards. Control signals from the computer 46, as will be described, are generated by a program running on that computer, and data signals transferred from the sequential charge-counter 44 to the computer 46 are displayed on a CRT screen 49.

Figure 3:
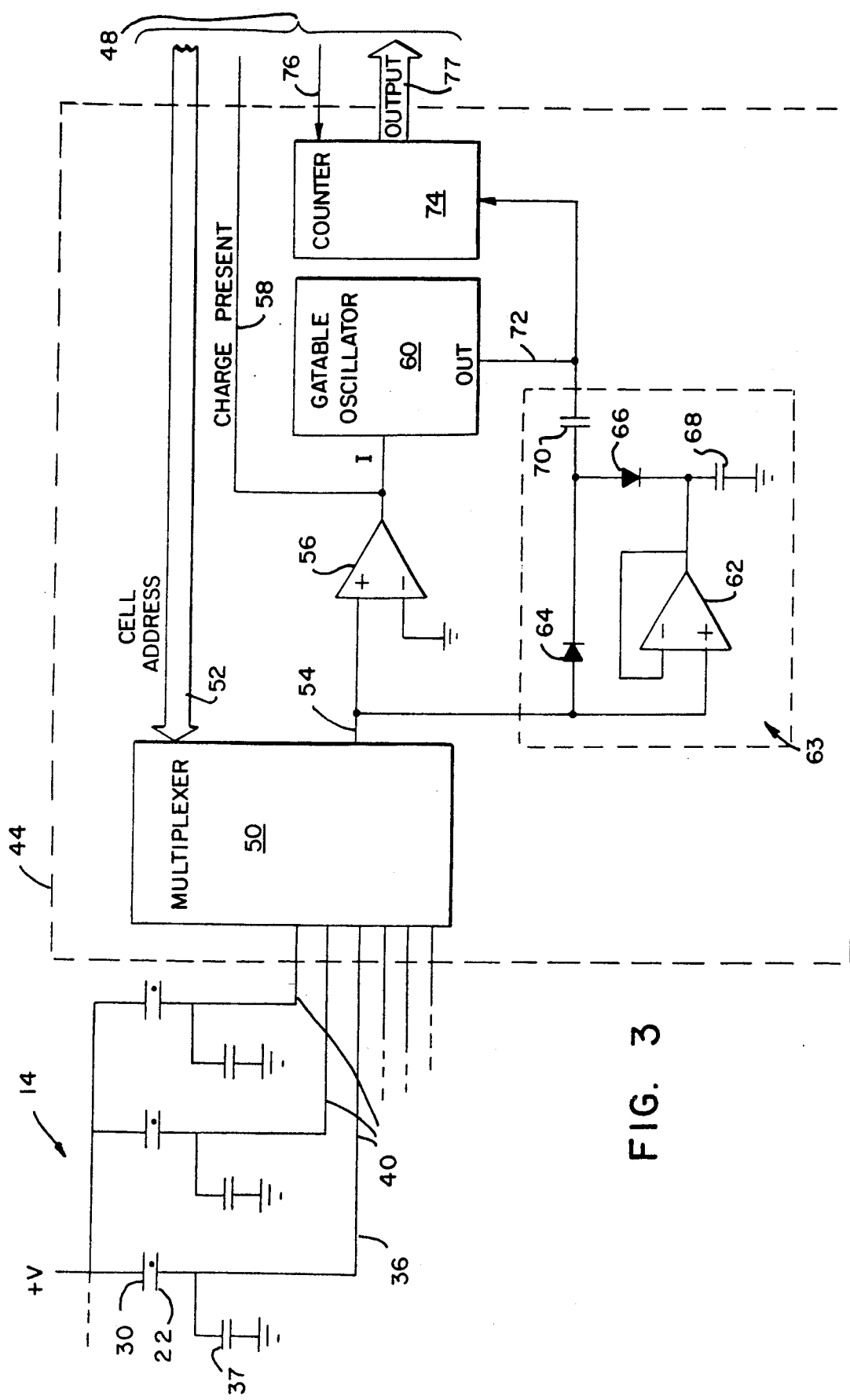
FIG. 3 is a simplified schematic diagram of the sequential charge-counter of FIG. 1.

Referring now to FIG. 3, the sequential charge-counter 44 receives the multiple conductors 40, each connected to an individual accumulating capacitor 37, at the inputs of a multiplexer 50. The multiplexer 50, in turn, connects one of the conductors 40 to a multiplexer output 54 as determined by a cell address 52 which is also received by the multiplexer 54. The cell address 52 is generated by the computer 46 and transmitted to the multiplexer 50 over the Bi-directional link 48. Multiplexer 50 may be a COS/MOS single sixteen channel multiplexer/demultiplexer such as Part No. IH6116 manufactured by Intersil of Sunnyvale, Calif.

During a measurement of the radiation profile of the radiation beam 12, the value of the cell address 52 will be incremented from zero to the maximum number of anodes 22 in the detector array 14. In doing so, the accumulating capacitor 37 of each anode 22 will be, in turn, connected to the multiplexer output 54. Multiplexer 50 employs COS/MOS technology to provide an ohmic connection between the multiplexer output 50 and the selected conductor 40 attached to a particular anode 22.

The multiplexer output 50 is received by the positive input of a high impedance buffer amplifier configured as a comparator 56. The output of this comparator 56 produces a "charge present" signal 58 having a positive value if there is a charge on the accumulating capacitor 37 selected by multiplexer 50. This charge present signal 58 is received by the computer 46 and when low (indicating no charge is present) it signals the computer when to increment the cell address 52 to measure the charge on the next accumulating capacitor 37.

The charge on the accumulating capacitor 37 selected by the multiplexer 50, through multiplexer output 54, is received by charge pump 62 comprised of a high impedance operational amplifier 62, diodes 64 and 66 and capacitors 68 and 70. Specifically, the noninverting input of the operational amplifier 62 is connected to the multiplexer output 54 as is the anode of diode 64. The inverting input of the operational amplifier 62 is connected to its output to configure the operational amplifier in a unity gain buffer configuration. The output of the operational amplifier 62 is also connected to the junction of the cathode of diode 66 and capacitor 68. The remaining lead of capacitor 68 is connected to ground whereas the anode of diode 66 is connected to the cathode of diode 64 and to one lead of capacitor 70. As will be explained, the capacitor 70 is used to draw off increments of charge from the accumulating capacitor 37 and henceforth will be termed "measuring" capacitor 70. The remaining lead of the measuring capacitor 70 is connected to the output of a gatable oscillator 60.

The charge pump 63 provides, at the junction of diodes 64 and 66, a voltage substantially equal to the voltage on the accumulating capacitor 37 connected to the multiplexer output 54. During the charge pumping operation, current may be received from the accumulating capacitor 37 by the measuring capacitor 70, through diode 64, and current may be discharged from the measuring capacitor 70 through diode 66 to the low impedance output of the operational amplifier 62. Capacitor 68 serves to improve the effective high frequency output impedance of the operational amplifier 62.

In operation, when the accumulating capacitor 37, selected by the multiplexer 50, has sufficient charge to raise its voltage above a predetermined minimum, dictated by the switching threshold of comparator 56, the output of comparator 56 goes high activating the gatable oscillator 60. The gatable oscillator 60, when so activated, produces a square wave at its output 72. It will be understood from the following description, that the output of the oscillator need not be a true square wave but may be any periodic waveform having an essentially constant wave shape.

Upon the activation of gatable oscillator 60, its output 72 rises to a peak value and current flows out of capacitor 70 through diode 66 to establish a voltage across measuring capacitor 70 defined by the difference between the peak value of the output of the gatable oscillator 72 and the voltage on the accumulating capacitor 37 as reproduced at the junction of diodes 64 and 66. The output 72 of the gatable oscillator 60 then falls to its lowest value drawing a small portion of the charge off of accumulating capacitor 37 and onto measuring capacitor 70. It will be understood that the amount of charge drawn off of accumulating capacitor 37 is proportional to the value of capacitor 70 and the difference between the highest and lowest voltage value of the output 72 of the gatable oscillator 60. Both of these quantities are substantially constant.

When the output 72 of gatable oscillator 60 rises again to its peak value, this charge drawn onto measuring capacitor 70 is discharged through diode 66 into the low impedance output of operational amplifier 62, re-establishing the voltage across measuring capacitor 70 as the difference between the voltage at the multiplexer output 54 (reflecting the voltage on the accumulating capacitor 37) and the peak value of the output 72 of gatable oscillator 60.

Thus, with each cycle of the output 72 of gatable oscillator 60 from peak value to lowest value to peak value, an essentially constant increment of charge is removed from the accumulating capacitor 37. Ultimately, after a number of cycles, all of the charge on accumulating capacitor 37 will be drawn off and the voltage on the accumulating capacitor 37 will drop below the predetermined minimum determined by comparator 56. At this time the gatable oscillator 60 is deactivated by the output of comparator 56. The number of cycles of the output 72 of gatable oscillator 60 prior to the discharge of accumulating capacitor 37 is counted by a counter 74 having an input connected to the output 72 of the gatable oscillator 60.

The output 77 of the counter 74 is connected to the Bi-directional link 48 to be read by the computer 46 and represents a quantification of the amount of charge accumulated on accumulating capacitor 37. In turn, this charge reflects the total radiation received over the time by the detector array 14 since accumulating capacitor 37 was last discharged by charge pump 63.

It will be understood that because the charge pump 63 measures the amount of charge on the capacitor 37, the actual value of capacitor 37, which directly affects the voltage on that capacitor, is largely immaterial. Further, the use of multiplexer 50 allows a single charge pump 63 to be employed, thus the values of the components of the charge pump 63 and in particular measuring capacitor 70 need not be matched to other components and need only be stable with time. The expense of the comparator 56, the charge pump 63 and the gatable oscillator 60 is independent of the number of anodes 22 used to measure the radiation beam 12 thus allowing an inexpensive implementation of a detector array 14 having a large number of measuring anodes 22.

In a typical measuring sequence as driven by computer 46, the computer 46 outputs a cell address 52 and reads the charge present signal 58 to see if significant charge has accumulated on the selected accumulating capacitor 37 of that anode 22. If so, the computer 46 waits for the charge present signal 58 to again drop to zero indicating the charge on the accumulating capacitor 37 has been fully depleted by charge pump 63. At this time the output of counter 74 is read to obtain a number indicating the amount of charge transferred from accumulating capacitor 37.

Counter 74 is then reset by the computer 46, through reset line 76, and the next anode 22 and accumulating capacitor 37 is selected by incrementing the cell address 52 to the multiplexer 50.

The value of the counter 74 for each anode 22 is stored in the computer 46 in a numerical array as will be well understood by those of ordinary skill in the art. This array may be processed to provide a display of the intensity of the radiation beam over the area defined by the common cathode 18 and to compute the mean values of the radiation, and the standard deviation from this mean, or other well known statistical measures.

It will be understood that the value of counter 74 obtained for each anode 22 will be proportional to both the intensity of the radiation 12 and the period of time in between the sampling and depletion of accumulating capacitor 37 by the multiplexer 50 and charge pump 63. Generally, variations in the measured radiation valves 74 will be minimized by sampling each anode 22 at regularly spaced intervals. It will be understood, however, that the sensitivity of the various anodes 22 may be varied by varying this sampling period if so desired. This variation is limited only by the constraints that sufficient time must pass so that the charge accumulated on accumulating capacitors 37 is commensurate with the range of the selectable charge-counter and thus neither too little to provide adequate resolution nor too high so as to be outside the range of the operational amplifiers 62 and 56, for example.

The multiplexor 50 and the sequential scanning of the cells of the detector array 14, makes it possible to share one computer 46 among a number of charge counters 44 and detector arrays 14 each located remotely, for example, in different rooms holding different pieces of equipment. In this case, the cell address 52 employs additional address bit denoting the address of the desired charge counter 44 so that the computer 46 selects not only among different cells of the detector array 14 but among different detector arrays 14 as well.

Several cycles of measuring the charge on the various accumulating capacitors 37 may be used and the values from counter 74 averaged to produce improved precision. Further, variations in the sensitivity of the anodes 22, caused by geometrical or other considerations, may be accommodated by multiplying each of the count values received from counter 74 by a weighting value from a table stored in the memory of the computer 46, each weighting value associated with the particular anode 22, so as to improve the uniformity of the measurement produced by this system.

A preferred embodiment of the invention has been described, but it should be apparent to those skilled in the art that many variations can be made without departing from the spirit of the invention. For example, the spacing and orientation of the channels may be adjusted to accommodate other x-ray scanning systems and the number of ionization cells may be varied as needed. As will be understood to those of ordinary skill in the art, a common anode and multiple cathodes may be used instead of the common cathode system described. In order to apprise the public of the various embodiments that may fall within the scope of the invention, the following claims are made.

I claim:

1. A radiation detector having a plurality of radiation sensitive cells for characterizing a radiation beam over an area, comprising:

charge generation means associated with each cell for generating an electrical charge related to the radiation received by the cell;

accumulating capacitor connected to each charge generation means for accumulating the generated electrical charge;

a charge-counter for receiving a charge and producing a magnitude signal indicating the amount of that charge, the charge counter including:

a voltage detector for detecting the presence of at least a predetermined amount of charge on an accumulating capacitor to produce a charge present signal;

a measuring capacitor for being connected to and disconnected from the accumulating capacitor;

an oscillator receiving the charge present signal and for repeatedly connecting and disconnecting the measuring capacitor to and from the connected accumulating capacitor, during a cycle, so that charge may move between the connected accumulating capacitor and the measuring capacitor when they are connected only so long as the charge present signal is present;

a bias means for restoring a substantially constant voltage difference between the accumulating capacitor and the measuring capacitor when the measuring capacitor is disconnected to provide a substantially constant amount of charge flow between the accumulating capacitor and the measuring capacitor each time they are connected; and counter means connected to the oscillator and the voltage detector for counting the total number of connections and disconnections of the measuring capacitor during the charge present signal;

a multiplexer for connecting each accumulating capacitor in sequence to the charge-counter for sequentially measuring the charge accumulated on the accumulating capacitor to produce a magnitude signal associated with each accumulating capacitor.

2. The radiation detector as recited in claim 1 wherein the charge generation means comprise:

a substantially planar first electrode having a biasing voltage and defining a first charged surface subtending some area of the radiation beam;

a plurality of substantially planar second electrodes electrically isolated from one another together comprising a second charged surface spaced from the first surface, the space between the first and second surfaces defining an interception volume, each second electrode having connector means for communicating a charge to a corresponding accumulating capacitor; and an ionizing gas contained within the interception volume to communicate charge between the first and second surfaces when ionized by radiation.

3. The radiation detector as recited in claim 2 wherein the planar first and second electrodes comprise nonconducting substrates with etchable copper cladding.

4. The radiation detector as recited in claim 2 wherein the interception volumes are substantially equal among the second electrode.

5. The radiation detector as recited in claim 2 wherein the second electrode are arranged in rectilinear rows and columns to cover substantially the entire area.

6. The radiation detector as recited in claim 1 wherein the multiplexer provides an ohmic, bi-directional connection between a connected accumulating capacitor and the charge-counter.

7. The radiation detector as recited in claim 1 including:

a computer controlling the multiplexer and receiving the magnitude signals for each accumulating capacitor and for adjusting the magnitude signal by a predefined adjustment value contained in a look-up table having values dependent on the particular cell and accumulating capacitor, to produce an adjusted magnitude value for each accumulating capacitor; and a statistical processor for performing statistical analysis of the adjusted magnitude values.

8. In a radiation detector having a charge generating means for generating a charge related to the received radiation and an accumulating capacitor for collecting said charge, a charge-counter for measuring the accumulated charge and hence the received radiation, the charge-counter comprising:

a voltage detector for detecting the presence of at least a predetermined amount of charge on the accumulating capacitor to produce a charge present signal;

a measuring capacitor for being connected to and disconnected from the accumulating capacitor;

an oscillator receiving the charge present signal and for repeatedly connecting and disconnecting the measuring capacitor to and from the accumulating capacitor, during a cycle, so that charge may move between the accumulating capacitor and the measuring capacitor when they are connected only so long as the charge present signal is present;

a bias means for restoring a substantially constant voltage difference between the accumulating capacitor and the measuring capacitor when the latter is disconnected to provide a substantially constant amount of charge flow between the accumulating capacitor and the measuring capacitor when they are connected; and counter means connected to the oscillator and the voltage ionization chamber for counting the total number of cycles of connections and disconnections of the measuring capacitor during the gating signal.

9. A radiation detection system comprising:

at least one radiation detector having a plurality of radiation sensitive cells for characterizing a radiation beam over an area, including:

charge generation means associated with each cell for generating an electrical charge related to the radiation receiving by the cell and subject to a sensitivity variation;

accumulating capacitor connected to each charge generation means for accumulating the generated electrical charge;

a charge-counter for receiving a charge and producing a magnitude signal indicating the amount of that charge; and multiplexer for connecting each accumulating capacitor in sequence to the charge-counter for sequentially measuring the charge accumulating on the accumulating capacitor to produce a magnitude signal associated with each accumulating capacitor;

a controller connected to the charge counter of the radiation detector to receive the magnitude signal and for controlling the multiplexer for selectively reading the magnitude signal associated with a given cell for the selected one radiation detector; and the controller including a weight table having a weighting value associated with the given cell and a means for applying the weighting value to the magnitude signal to correct for the sensitivity variation associated with the cell.

* * * * *